(12) United States Patent
Gulari et al.

(10) Patent No.: US 9,304,280 B2
(45) Date of Patent: Apr. 5, 2016

(54) COMPACT LENS SYSTEM AND ARRAY (71) Applicant: THE REGENTS OF THE UNIVERSITY OF MICHIGAN, Ann Arbor, MI (US)

(72) Inventors: Mayurachat Ning Gulari, Ann Arbor, MI (US); Mostafa Ghannad-Rezaie, Ann Arbor, MI (US); Anurag Tripathi, Ann Arbor, MI (US); Nikolaos Chronis, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 40 days.

(21) Appl. No.: 14/207,852

(22) Filed: Mar. 13, 2014

(65) Prior Publication Data

US 2014/0268319 A1 Sep. 18, 2014

Related U.S. Application Data (60) Provisional application No. 61/781,944, filed on Mar. 14, 2013.

(51) Int. Cl.
| | | |
|---|---|---|
| *G02B 7/02* | (2006.01) | |
| *G02B 21/33* | (2006.01) | |
| *G02B 3/00* | (2006.01) | |
| *G02B 21/36* | (2006.01) | |
| *G01N 15/14* | (2006.01) | |
| *G01N 21/64* | (2006.01) | |

(52) U.S. Cl.
CPC ............ *G02B 7/027* (2013.01); *G01N 15/1436* (2013.01); *G01N 21/6458* (2013.01); *G02B 3/0056* (2013.01); *G02B 21/365* (2013.01)

(58) Field of Classification Search
CPC ...... G02B 3/00; G02B 3/0006; G02B 3/0056; G02B 3/0075; G02B 7/027; G02B 9/02; G02B 13/0085; G02B 13/24; G02B 21/33; G02B 21/36; G02B 27/1066; G02B 27/123; G01N 15/1436; G01N 21/253; G01N 21/6428; G01N 21/6447; G01N 21/645–21/6456

See application file for complete search history.

(56) References Cited

U.S. PATENT DOCUMENTS

| | | | |
|---|---|---|---|
| 4,465,621 A | * | 8/1984 | Sacher ........................ 252/582 |
| 7,023,622 B2 | | 4/2006 | Liang |

FOREIGN PATENT DOCUMENTS

WO   WO-2013120091 A1   8/2013

OTHER PUBLICATIONS

Chronis et al., "Tunable liquid-filled microlens array integrated with microfluidic network," Optics Express, vol. 11, No. 19, Sep. 22, 2003, pp. 2370-2378.*

(Continued)

*Primary Examiner* — Stephone B Allen
*Assistant Examiner* — Adam W Booher
(74) *Attorney, Agent, or Firm* — Harness, Dickey & Pierce, PLC (57) ABSTRACT

A compact lens system for imaging a sample comprising a substrate having a well formed therein. Index matching material is disposed in the well and a lens member is further disposed in the well in optical contact with the index matching material disposed in the well. A spacer member extends from at least one of the substrate and the lower transparent member to define a spacing from a focal point of the lens member, wherein the lens member and index matching material cooperate to image a sample disposed below the lower transparent member.

19 Claims, 8 Drawing Sheets

(56) References Cited

OTHER PUBLICATIONS

Gulari et al., "Microfluidic-Based Oil-Immersion Lenses for High Resolution Microscopy," 16th International Conference on Miniaturized Systems for Chemistry and Life Sciences, Okinawa, Japan, Oct. 28-Nov. 1, 2012, pp. 49-51.*

Arpa, A., Wetzstein, G., Lanman, D., and Raskar, R., "Single Lens Off-Chip Cellphone Microscopy," Computer Vision and Pattern Recognition Workshops (CVPRW), 2012 IEEE Computer Society Conference on Jun. 16-21, 2012, pp. 23-28.

Bogoch, I., et al., "Short Report: Mobile Phone Microscopy for the Diagnosis of Soil-Transmitted Helminth Infections: A Proof-of-Concept Study," Am. J. Trop. Med. Hyg., 88(4), 2013, pp. 626-629.

Cybulski, J., Clements, J., and Prakash, M., "Foldscope: Origami-based paper microscope," PLoS ONE, 2014, 36 pgs.

Ghosh, K., et al., "Miniaturized integration of a flouresence microscope," Nature Methods, vol. 8, No. 10, Oct. 2011, pp. 871-882.

McCall, B., et al., "Toward a low-cost compact array microscopy platform for detection of tuberculosis," Tuberculosis, 91, (2011), pp. S54-S60.

Orth, A. and Crozier, K., "Microscopy with microlens arrays: high throughput, high resolution and light-field imaging," (Jun. 4, 2012), Optics Express, vol. 20, No. 12, 13522-13531.

Pang, S., Han, C., Erath, J., Rodriguez, A. and Yang, C., "Wide field-of-view Talbot grid-based microscopy for multicolor flourescence imaging," (Jun. 17, 2013), Optics Express, vol. 21, No. 12, p. 14555-14565.

Smith, Zachary J., Chu, Kaiqin, Espenson, Alyssa R., et al., "Cell-Phone-Based Platform for Biomedical Device Development and Education Applications," (Mar. 2011), PLoS ONE, 6 (3), 11 pages.

Tripathi, A. and Chronis, N., "A doublet microlens array for imaging micron-sized objects," (Sep. 21, 2011), J. Micromech Microeng., 21(10), 12 pages.

* cited by examiner

COMPACT LENS SYSTEM AND ARRAY

CROSS-REFERENCE TO RELATED APPLICATIONS

This application claims the benefit of U.S. Provisional Application No. 61/781,944, filed on Mar. 14, 2013. The entire disclosure of the above application is incorporated herein by reference.

GOVERNMENT INTEREST

This invention was made with government support under OD006458 awarded by the National Institutes of Health. The government has certain rights in the invention.

FIELD

The present disclosure relates generally to imaging and, more particularly, relates to submicron resolution imaging of bacteria, cells, microorganisms, whole tissue, and the like in bright field, dark field and fluorescent image modes in multiple locations simultaneously using a compact lens system and array.

BACKGROUND AND SUMMARY

This section provides background information related to the present disclosure which is not necessarily prior art. This section also provides a general summary of the disclosure, and is not a comprehensive disclosure of its full scope or all of its features.

Optical microscopy is the gold standard for the visualization of biological entities as well for the identification, diagnosis and monitoring of many diseases such as sickle-cell disease, malaria, and tuberculosis. High-end optical systems that achieve submicron resolution imaging rely on multi-element objective lenses that are expensive and bulky.

Biological imaging systems consist, in a broad sense, of a microscope for magnifying the section of the sample, a light source to illuminate the sample, and a camera which can be attached to the eyepiece of the microscope to take digital or analog images of the section of the sample which is being observed. For most applications, resolutions on the order of one micron or better are needed for observing fine details of the sample as well as for carrying out tasks such as counting of cells within a given sample volume. This is normally achieved by employing expensive high magnification immersion objectives for the microscopes, which can cost several thousand dollars each.

The large physical size of many microscopes is an impediment to making measurements in controlled environments, such as incubators or with living laboratory animals, such as mice, rats or guinea pigs.

Stereoscopes normally have a single optical train of lenses, prisms, and mirrors for collecting the light from the sample and forming an image at the image plane or the eye of the observer. Single train nature of the microscope combined with a high-resolution, high numerical aperture requirement results in immersion objectives which have very narrow fields of view that limit the observation area to about a hundred microns in diameter. This limitation prevents simultaneous observation of a large area of the sample with high resolution. To observe other parts of the sample, the sample has to be physically moved and brought into focus again.

Ball lenses have been used in optics for laser collimating, fiber coupling, and endoscopic imaging. Lately, ball lenses have been used to constructing miniaturized microscopes. However, the resolution and image quality of the previous attempt at making simple imaging systems with ball lenses was not very successful—maximum resolution achieved was greater than one micron and the image quality was poor due to its construction.

Miniature microscope lenses were made by essentially miniaturizing the microscope objectives (U.S. Pat. No. 7,023, 622). Arrays of these miniaturized objective lenses were used to make scanning array microscope systems. However, the cost of these systems was prohibitively high.

The present teachings address the shortcomings of the prior art, providing a novel and inexpensive imaging system, which costs at least an order of magnitude less and is smaller by a similar amount while providing as high a resolution as the best immersion microscope objectives.

According to the principles of the present teachings, a compact lens system is provided for imaging a sample in some embodiments. The compact lens system comprises a substrate having a well formed therein, the well having an open first end and an open second end wherein the second end opposing the first end and being in communication therewith. The system further comprises a lower transparent member extending along a lower surface of the substrate, thereby enclosing the open second end of the well, and an index matching material disposed in the well. A lens member is disposed in the well and in optical contact with the index matching material disposed in the well. A refractive index of said lens member being generally equal to a refractive index of said index matching material. A spacer member extends from at least one of the substrate and the lower transparent member to define a spacing from a focal point of the lens member, wherein the lens member and the index matching material cooperate to image a sample disposed below the lower transparent member.

In some embodiments, a compact lens array system for imaging a sample is provided. The compact lens array system comprises a substrate having a plurality of microwells disposed in an array of rows and columns, each of the microwells having an open first end and an open second end. The second end opposing the first end and being in communication therewith. A lower transparent member extends along a lower surface of the substrate enclosing the open second end of each of the microwells. A reservoir is provided and a microfluidic channel fluidly couples at least one row of the array of microwells to the reservoir. An index matching material is disposed in the reservoir and in fluid communication with the at least one row of the array of microwells via the microfluidic channel. A plurality of lens members are disposed in each of the microwells in optical contact with the index matching material disposed in the microwells. A refractive index of each of the plurality of the lens members is generally equal to a refractive index of the index matching material. A spacer member extends from at least one of the substrate and the lower transparent member to define a spacing from a focal point of the plurality of lens members, wherein the lens members and the index matching material cooperate to image a sample disposed below the lower transparent member.

In some embodiments of the present teachings, a novel microfluidic-based device is provided for obtaining a low-cost, high-NA array of miniaturized ball lenses for imaging biological samples. In some embodiments, lenses are made of high index of refraction material. The lenses can be placed on top of an array of liquid-filled lens wells that are microfabricated as a holder platform. The precise platform configuration enables easy assembly and effective holding/retention. Moreover, the Microfluidic-based Oil-Immersion (μOIL) lens array or chip of the present teachings provides optical performance (resolution, NA) equivalent to the performance of a conventional microscope objective, while also enabling multiple wide field of view imaging as its size can be easily scaled up. A low-cost, compact, high-resolution, high numerical aperture optical imaging system using the compact lens system for counting cells is provided.

The present teachings, in some embodiments, employ single ball lens optics to overcome the cost and complexity issues associated with compound lens microscope objectives. Higher numerical aperture and submicron resolution is achieved by using semiconductor manufacturing techniques to make a microfluidic lens holder which simultaneously positions the lens at a precise distance from the sample and immerses half of the ball lens, for example, in an index matching fluid effectively creating an immersion microscope objective with resolution comparable to the best compound microscope objectives. By having an array of miniball lenses, it is possible to simultaneously image many different samples with equal resolution simultaneously or image different parts of a large sample with high resolution. A sample cartridge is inserted between the illumination source and the lens array. In some embodiments, an LED light source, wavelength filters and imaging sensor can be used to enable both bright field and fluorescence imaging.

In some embodiments, the imaging sensor located in the image plane of the mini ball lenses records digitally all of the images formed by the mini lenses simultaneously with approaching the diffraction limit. The advantages of such a system is obvious to those skilled in the art: By way of non-limiting example, it is possible to follow different events taking place at the cellular or subcellular level, to count red and white blood cells or their subpopulations with good statistics, observe response of cells to different drugs, record time dependent changes occurring in cells exposed to different environments, observe growth of different embryos, white and red blood cell counting and many similar phenomena too many to list here. Furthermore, the small size and weight of the compact lens system, around one cubic inch in some embodiments, allows its use in remotely monitoring samples where large bulky microscopes cannot be used.

The compact lens system of the present teachings can be part of a lab-on-chip system or it can be used as an add-on module in low cost stereoscopes to enable high resolution imaging of small objects in the lab, in the doctor's office, or in the field. The compact lens system can be integrated to a CMOS (complementary metal oxide semiconductor) commercial sensor for a miniature wireless microscope system to monitor biological development in an incubator, a compact imaging system for cell counters, or can be used as an optical part of Digital Pathology Scanner.

The present teachings provide a number of advantages, including providing an array of mini objectives which give multiple field of views whereas expensive bench top microscopes can only see one field of view, only one objective at a time. Moreover, each objective mini-lens of the present teachings provides high numerical aperture and high resolution (~0.5 microns) and an inexpensive and small foot print lens holder. This lens array chip is 1*1*0.2 cm³ volume, which make it easy to integrate into a compact & light weight imaging system. Furthermore, the present teachings can be used in a wide range of optical imaging applications, such as Cell Counters, Point of Care Diagnostic systems, Miniature microscope systems that can be used in incubators, and high resolution Digital Pathology Scanners.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As mentioned herein, optical microscopy is the gold standard for the visualization of biological entities as well for the identification, diagnosis and monitoring of many diseases such as sickle-cell disease, malaria, and tuberculosis. High-end optical systems that achieve submicron resolution imaging rely on multi-element objective lenses that are expensive and bulky. In recent years, there has been an increased interest in integrating optical components on-chip. The development of micro-optical modules typically involves the challenging task of lens miniaturization if superb imaging quality needs to be maintained.

Optical imaging systems with submicron resolution typically require the use of expensive, high numerical aperture (NA) microscope objective lenses. However, according to the principles of the present teachings, a compact lens system 10 is provided that can, in some embodiments, perform submicron and wide field of view imaging. In some embodiments, compact lens system 10 can comprise high index of refraction, oil-immersion ball mini-lenses 12 having NA as high as 1.2 and therefore submicron optical resolution. The compact lens system 10 can be part of a lab-on-chip system and/or used as an add-on module in low cost stereoscopes to enable high resolution imaging of biological samples in the lab, in the doctor's office, or in the field.

The present teachings further demonstrate a novel microfluidic-based approach for obtaining a low-cost, high-NA array of miniaturized doublet lenses for imaging biological samples. As will be discussed in greater detail, the lenses of the present teachings can be made of high index of refraction sapphire lenses. These lenses can be placed on top of an array of oil-filled lens wells that are microfabricated on a silicon chip. The resultant Microfluidic-based Oil-Immersion Lens (µOIL) array 10 provides optical performance (resolution, NA) equivalent to the performance of a conventional microscope objective and further enables wide field of view imaging as its size can be easily scaled up. As will be appreciated by the present disclosure, variations of materials and configurations are envisioned in connection with the present teachings.

Design

Figure 1A:
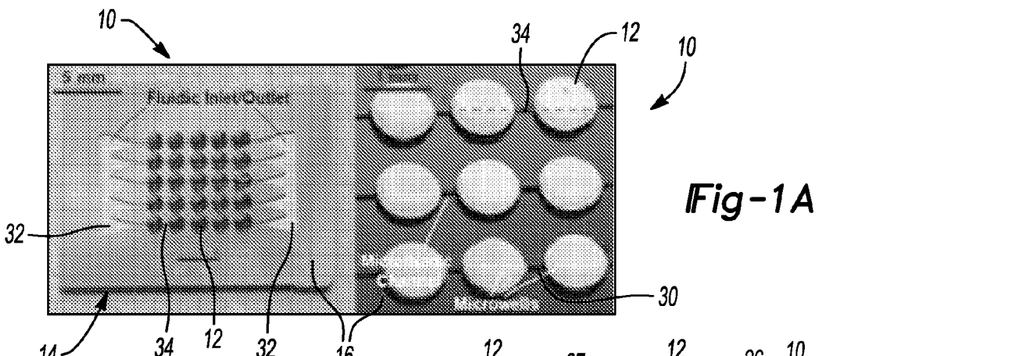
FIG. 1A is a plan view of a compact lens system (or compact lens system) according to the principles of the present teachings, including an enlarged view thereof.
Figure 1B:
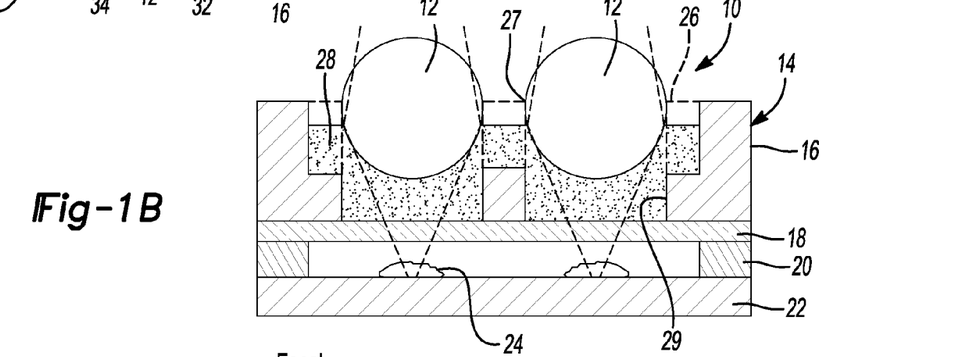
FIG. 1B is a schematic cross-sectional view of the compact lens system.

In some embodiments, as illustrated in FIGS. 1A and 1B, the compact lens system 10 can comprise a plurality of lenses 12 disposed in a substrate array 14. The substrate array 14 can comprise base substrate 16, such as a silicon chip, having a lower transparent member 18, such as a coverslip, thin film, membrane (e.g. silicon nitride membrane), and one or more spacer members 20 disposed below the lower transparent member 18. Spacer members 20 are sized and configured to rest upon a sample holder 22 containing a sample-to-be-imaged 24. In some embodiments, space members 20 can be integrally formed with lower transparent member 18 and/or base substrate 16.

It should be noted that although the present teachings are described in detail including a plurality of lenses 12 disposed in an array format, alternative embodiments are anticipated, disclosed, and illustrated having only a single lens element, together with the associated structure. Therefore, the present invention should not be regarded as being limited to any embodiment requiring a plurality of lens unless otherwise specifically claimed. In the interest of brevity, the present teachings will be described in detail in conjunction with an array format, however it is believed to be well within the skill of those reading the present disclosure that the device can be scaled down to a single lens arrangement.

In some embodiments, each of the plurality of lenses 12 is disposed in a lens well 26, or "microwell" in the case of micro-sized lenses 12, formed in base substrate 16. Each lens well 26 includes a top opening 27 and a bottom opening 29, and being open therebetween. In some embodiments, top opening 27 defines a width or diameter that is greater than a width or diameter of bottom opening 29. Lens well 26 retains an index matching material 28, such as a liquid, monomer, polymer, or other material, therein that optically contacts at least a portion of a respective one of the plurality of lenses 12 disposed in lens well 26.

In some embodiments, the plurality of lenses 12 can comprise a plurality of sapphire ball mini-lenses. In some embodiments, each of the plurality of sapphire ball mini-lenses can measure about 1 mm in diameter and have a refractive index of 1.77. In some embodiments, the plurality of lenses 12 can be off-the-shelf, non-microfabricated lenses.

However, in some embodiments, each of the plurality of lenses 12 can be made of a transparent high refractive index material that can transmit light, has one or both side convex shape design to focus/converge light to a point. In some embodiments, the diameter of each of the plurality of lenses 12 can be between 10 microns to 5 mm. It should be appreciated that the plurality of lenses 12 can define any one of a number of physical lens shapes, such as sphere, half sphere, biconvex, plano-convex, doublet, aspheric, achromatic shape, or the like. Lens can include one or multiple elements. Each of the plurality of lenses 12 can be made of any high refractive index (n>1) material, such as, but not limited to, glass, Fused Silica, sapphire, polymer, Germanium (Ge), Silicon (Si), or Zinc Selenide (ZnSe). It should be understood that lenses can be used individually or in a group (array). It should also be understood that lens 12 can define a refractive index in the range of 1.5 to 1.8.

In some embodiments, substrate array 14 can comprise the plurality of lens wells 26 arranged in an array. More particularly, in some embodiments, the substrate array 14 can comprises a 5×5 array of wells 26 that are each fluidly coupled or connected through an open-air microfluidic network 30 that distributes the index matching material 28 equally to each lens well 26 in the entire array. The microfluidic network 30 can include a fluidic reservoir 32 on at least one end and a plurality of microfluidic channels 34 in fluid communication between fluidic reservoir 32 and at least one of the plurality of lens wells 26. In some embodiments, a plurality of lens wells 26 can be fluidly coupled with fluidic reservoir 32 in series, thereby having a first fluidic reservoir 32 and a second fluidic reservoir 32 on opposing sides of the plurality of lens wells 26 and having each row of the plurality of lens wells 26 fluidly coupled via microfluidic channels 34 (See FIG. 1A).

In some embodiments, a cover system can be used to cover top opening 27 and/or microfluidic network 30. In some embodiments, cover system can include a thin film, e.g. parylene, to enclose the system and provide a barrier to outside contaminants and/or provide a means to seal the lens and assembly.

In some embodiments, each of the plurality of lenses 12 can define a diameter slightly larger than the diameter of the respective lens well 26 such that each of the plurality of lenses 12 sits generally above the lens well 26. In some embodiments, when lens wells 26 are filled with index matching material 28, lens 12 can be generally half immersed in index matching material 28 and half exposed to air. As a result, the index matching material 28/lens 12 combination acts as a doublet lens, resembling the hemispherical front lens of a high numerical aperture oil-immersion microscope objective.

In some embodiments, index matching material 28 defines a refractive index close or generally equal to the refractive index of the material of lens 12. In some embodiments, index matching material 28 can have a refractive index in the range of 1.3 to 1.8. In some embodiments, index matching material 28 can be an incompressible fluid that flows freely in microfluidic channels 34. In some embodiments, index matching index matching material 28 can be a monomer (e.g. liquid monomer) which can be polymerized in situ. In some embodiments, index matching material 28 can comprise a UV curable liquid photopolymer that is distributed via the microfluidic channels of the present teachings and then exposed to UV light. The UV light can initiate a curing process causing the liquid photopolymer to become solid. In some embodiments, the UV curable liquid photopolymer is Norland Optical Adhesive 61 available from Norland Products, which has a refractive index of 1.56 when cured. In some embodiments, index matching material 28 can comprise immersion oil. In some embodiment, this oil can have the same refractive index as the substrate material used on substrate array 14, such as lower transparent member 18. The refractive index of oil is approximately 1.5 to 1.6. However, alternative liquids can be used, including water (n=1.33) and/or UV curable polymer (n=1.5). The results show that using oil, water, monomer, or UV polymer provide higher image resolution compared to an air medium.

In some embodiments, substrate array 14 can further be configured and sized such that the combination of the plurality of lenses 12, index matching material 28, and lower transparent member 18 produce a focal length that is fixed to a corresponding physical distance of the plurality of lenses 12, lower transparent member 18, and spacer member 20 thereby resulting in a focal point coplanar with a lowermost plane of spacer member 20. In this way, in some embodiments, the geometry of the compact lens system 10 can be selected such that the focal length of compact lens system 10 (~620 μm, taken from the center of lenses 12) is located to clearly focus upon samples 24 below compact lens system 10 and, likewise, exit compact lens system 10 above in a converging fashion. In some embodiments, compact lens system 10 can produce an image at an image plane.

In operation, sample 24 is placed underneath the compact lens system 10 at a fixed distance, defined by the dimensions of compact lens system 10, from the doublet array. The sample 24 is then imaged through a 100 μm thick glass coverslip 18. The distance between the lenses 12 and the sample 24 which affects the magnification and the NA, is accurately defined by the thickness of the spacer member 20, which can comprise a photoresist film that is patterned on the backside of the glass coverslip 18.

It should be understood that in some embodiments, a thin film encapsulation can be placed on the top of compact lens system 10. The film is chosen so as not to interfere with optical performance, and yet can enhance the stability of the sapphire ball-lenses on the microfluidic platform.

Figure 2:
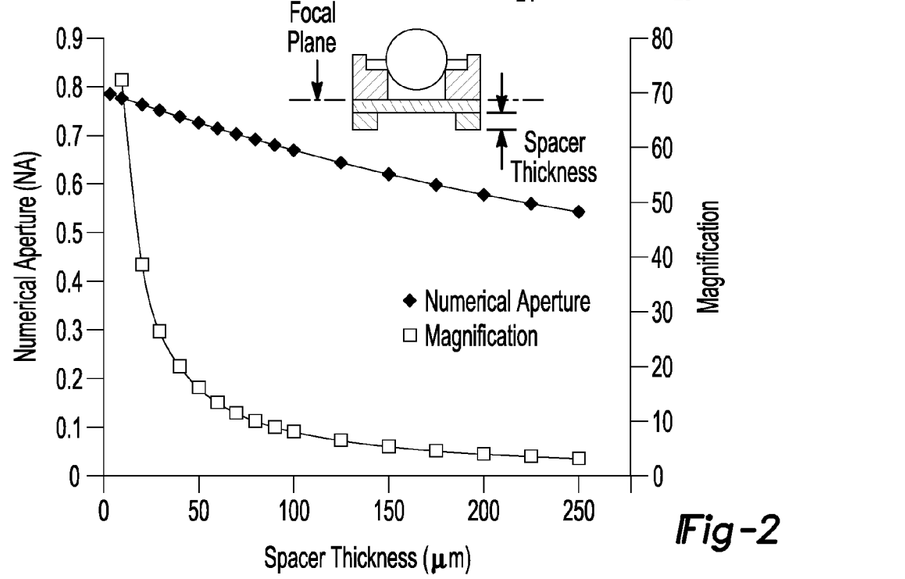
FIG. 2 is a graph illustrating numerical aperture (NA) and magnification versus spacer thickness in μm.

Construction of a compact lens system 10 can begin with an optical simulation (Oslo) to calculate the focal point, the NA, and magnification of the microlens chip (see FIG. 2). Then NA and magnification are plotted as a function to the distance of the sample from the focal plane of the array. That distance coinciding with the spacer thickness as the focal plane of the array is located at the backside of the glass coverslip. Assuming a minimum spacer thickness of 5-10 μm (e.g. when imaging a cell), the magnification and NA can reach a maximum value of ≥120× and ≥1.2, respectively. As the spacer thickness increases, there is a dramatic reduction in the magnification while the NA decreases almost linearly. The spacer thickness from our experiment is varied from 100 to 250 μm.

Microfabrication of the Compact Lens System

Figure 3:
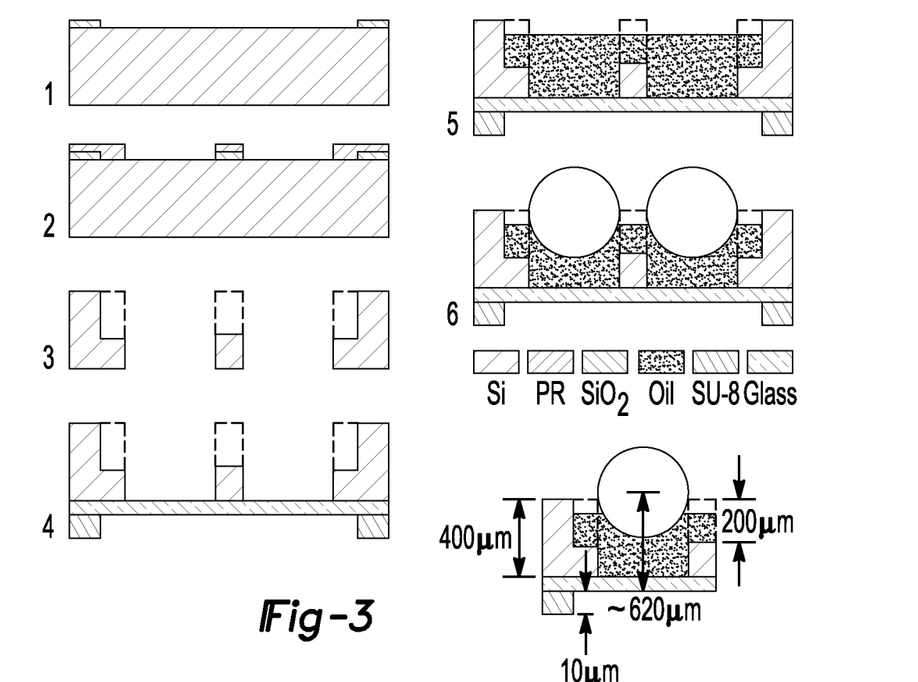
FIG. 3 is a series of schematic cross-sectional views illustrating the manufacturing steps of manufacturing the compact lens system according to the principles of the present teachings.

In some embodiments, the microfabrication of the compact lens system 10 is completed in the following steps as illustrated in FIG. 3. It should be understood, however, that alternative manufacturing techniques can be employed, including those using alternative materials such as plastic, metal, and the like. A manufacturing process using silicon can include:

1) a 200 nm thick silicon dioxide film is deposited and patterned on a 400 μm thick silicon wafer to define the microfluidic network;

2) a photolithographic step is then performed on a photoresist layer to define the lens well array;

3) a time-controlled deep reactive ion etching (DRIE) step is carried out to etch the wafer through;

4) a 100 μm thick glass coverslip, having a 10 μm thick SU-8 layer on its backside, is attached to the silicon wafer using epoxy;

5) the microfluidic network and the array are filled with immersion oil (refractive index of ~1.516); and 6) the ball mini-lenses are manually assembled on the oil-filled array.

Use with Stereoscope

Figure 4A:
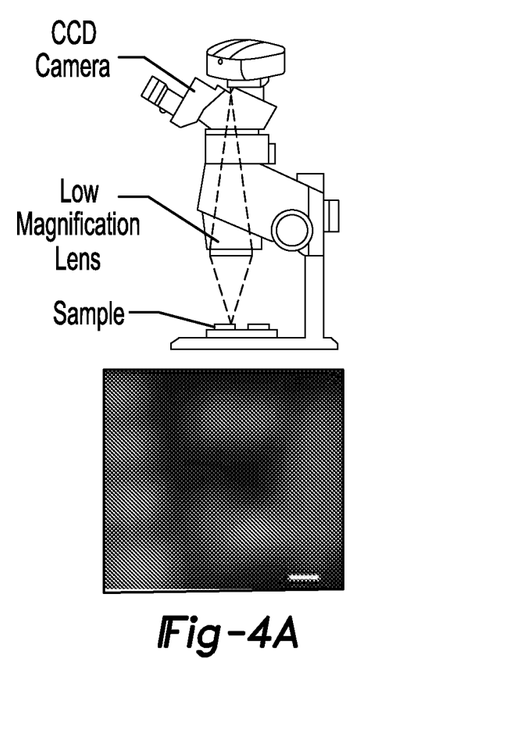
FIG. 4A is a schematic view of a conventional microscope and associated image capture of a resolution chart.
Figure 4B:
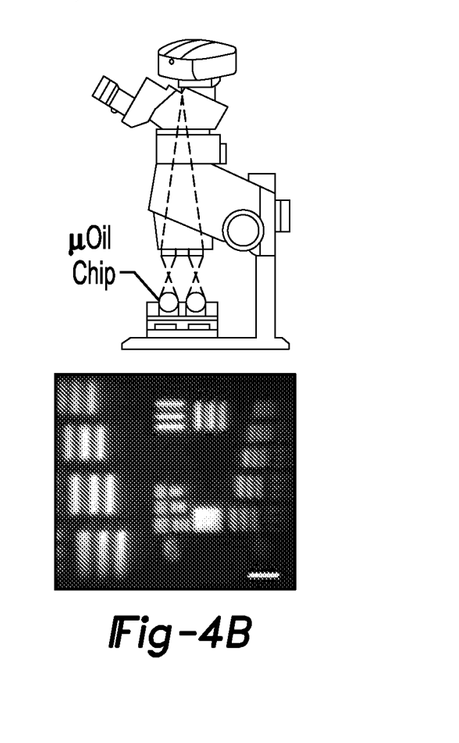
FIG. 4B is a schematic view of a microscope employing the compact lens system and associated image capture of a resolution chart.
Figure 5:
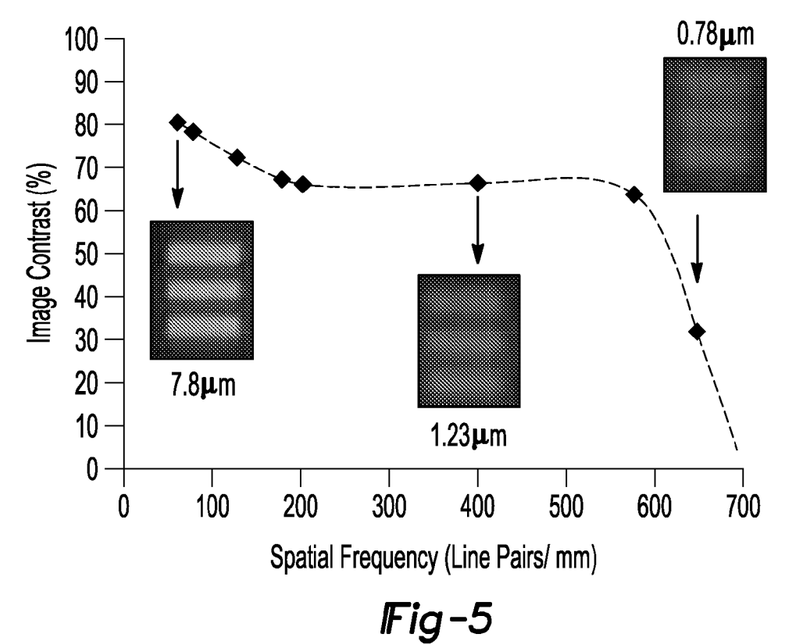
FIG. 5 is a graph illustrating image contrast versus spatial frequency of a resolution line pattern highlighting line pairs of three different widths (7.8 μm, 1.23 μm and 0.78 μm)
Figure 6A:
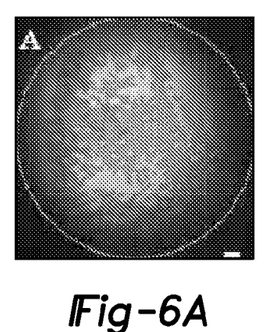
FIGS. 6A-6D are bright field images of microspheres (A) and blood cells (B), a fluorescence image of white blood cells (C), and C. elegans eggs in various developmental stages (D)
Figure 6B:
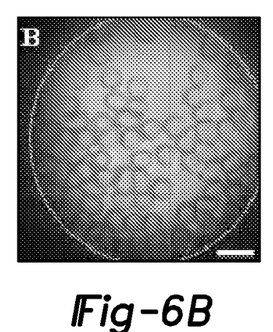
Figure 6C:
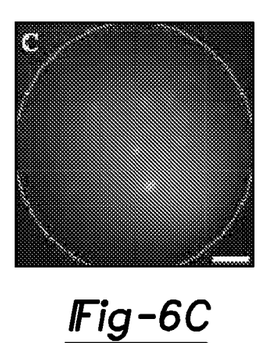
Figure 6D:
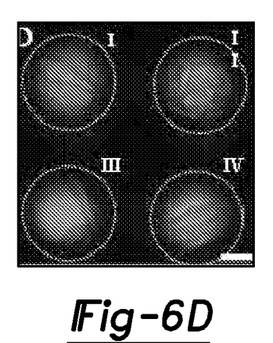

As illustrated in FIG. 4B, the compact lens system 10 can also be used as an add-on module in a low-cost, low NA stereoscope to achieve high resolution imaging compared to a conventional stereoscope (see FIG. 4A). Such a configuration can be useful in a resource-limited setting or in the doctor's office where a high-end microscope is not available. As illustrated in FIG. 5, the Modulation Transfer Function (MTF) of a stereoscope (Olympus sz61) using compact lens system 10 was obtained by imaging line pairs from a resolution test chart using a 10 μm spacer. Even the smallest line pairs of 0.78 μm line width were clearly distinguishable. Therefore, according to the principles of the present teachings, resolution can approach the theoretical limit.

As illustrated in FIG. 6, the ability of the combined system (e.g. stereoscope (Olympus sz61) using compact lens system 10) to image microspheres and cells was demonstrated in brightfield (transmission) and epi-fluorescence modes using a 10 μm spacer. In both cases, individual 2-μm diameter microspheres and blood cells were clearly visible. Finally, to demonstrate wide field of view imaging, the compact lens system 10 was used to image in vivo the nematode *C. elegans* at different developmental stages (FIG. 6D). The field of view was ~200 μm in diameter for each lens on the array. In this case, the spacer thickness was adjusted to ~210 μm in order to compensate for the thick worm body.

Discussion

While the top killer diseases in developed countries are heart diseases and cancers, the leading cause of death in developing countries are infectious diseases and indeed, the majority of infectious diseases can be prevented by proper diagnosis and treatments.

To design diagnostic technology for the developing world, it is critical to follow WHO guidelines for accessibility, specificity, ease to use, affordability, speed and robustness. In these requirements, it is natural for researchers to use microfluidics because microfluidic systems are compact, mass-producible, need low power, short processing times and can have high sensitivity at low cost. Microfluidic system can also potentially make a significant contribution in monitoring pathological conditions especially in resource-limited settings.

Flow cytometry and fluorescence microscopy are tools which are used extensively both in biomedical research and clinical diagnostics. Currently, fluorescence-based flow cytometers operating by laser light scattering and laser-induced fluorescence principles are the gold standard to provide accurate CD4+ T lymphocyte counting at high throughputs. Flow cytometers, although extremely accurate and high-throughput, are expensive, bulky instruments that require regular maintenance and well trained technicians to operate.

The significance of having a low cost high resolution imaging system, such as compact lens system 10, which can match the resolution of very expensive bulky microscopes and accuracy of flow cytometers for counting cells, cannot be under stated. The present teachings can be used in low resource settings as well as point of care with very low cost. The present teachings permit one to count red blood cells, white blood cells, identify abnormalities in the blood cells (sickle cell anemia, malaria etc.) instantly. In addition to the diagnostic applications, the present teachings can also be revolutionary in education and research. It will be a revolutionary instrument in research and educational laboratories. A compact system which can provide optical resolution down to the theoretical resolution limit and do it in a package even individual students can afford.

The present teachings provide a simple optical system consisting of spherical sapphire ball lenses placed on top of an array of index matching oil filled lens wells microfabricated on a silicon chip. In this configuration, the ball lenses act as an array of doublet lenses very similar to the immersion objectives of high resolution microscopes. This Microfluidic-based Oil-Immersion Lens (μOil) array system 10 provides optical performance (resolution, NA) equivalent to the performance of a conventional microscope objective but it also enables wide field of view imaging as its size can be easily scaled up by increasing the number of lenses in the array.

The present teachings also provide an opportunity to combine the compact lens system 10 with a low cost CMOS camera, a compact light source, and image analysis software for counting purposes. This compact (~3"×3"×3" in unoptimized prototype version) can be easily carried to use in diagnostic purposes in low resource settings.

The present teachings can be used in conjunction with fluorescent imaging using both total internal reflection as well as zero mode waveguide configurations. It is anticipated that the present system can be used to prepare disposable microfluidic sample preparation/handling chips to use with the integrated system so that no sample preparation will be required.

Additional Embodiments

Imaging System: Bright Field

Figure 7A:
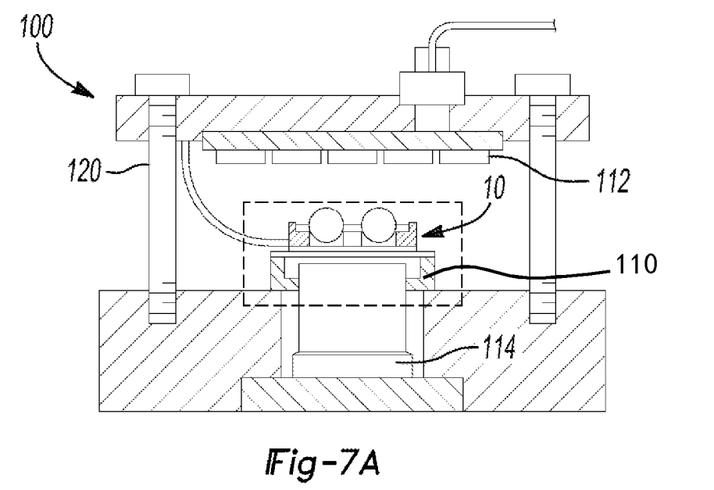
FIG. 7A is a schematic cross-sectional view of an imaging system employing the compact lens system.

In some embodiment, as illustrated in FIG. 7A, the present teachings provide a compact, high-resolution, optofluidic imaging system 100 for visualizing and counting red blood cells (RBC) employing compact lens system 10. It should be understood that the present system can be used for counting white blood cell, imaging biological specimens in a resource limited setting or at the doctor's office. In some embodiments, the system 100 has a footprint of 7 cm×7 cm and a total height of 6 cm.

Figure 7B:
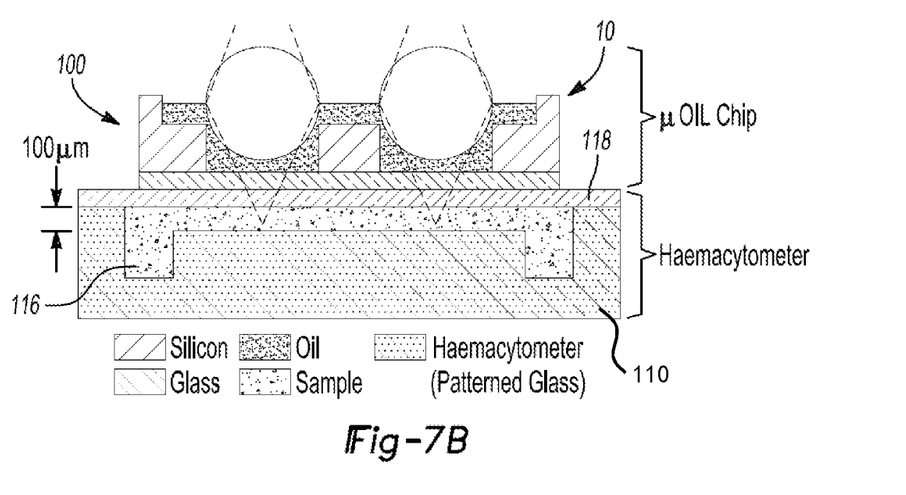
FIG. 7B is a schematic cross-sectional view of the compact lens system being used in conjunction with a haemocytometer.

In some embodiments, as illustrated in FIGS. 7A and 7B, imaging system 100 operates in bright field mode can comprises compact lens system 10, a commercially-available haemocytometer 110, CMOS sensor 112 (2.2×2.2 μm pixel size) and, a blue collimated LED 114. The haemocytometer 110 is a thick glass slide which forms a 100 μm microfluidic cell counting chamber 116 (known as the Neubauer chamber) when a glass coverslip 118 is placed on top of it. A custom-made plastic housing can be manufactured to secure all components in place, except the haemocytometer that is manually inserted into the housing from the side.

The haemocytometer containing the blood sample is illuminated by the LED (centered at 470 nm) from below. The transmitted light is collected by the high numerical aperture (NA) lenses of the compact lens system 10 and is focused on the CMOS sensor that is placed 3-4 mm above the compact lens system 10 (FIG. 7B). To achieve a sharp, well-focused image, the exact distance between the compact lens system 10 and the CMOS sensor is manually adjusted using a set of screws 120. Finally, the CMOS sensor is connected to a computer that acquires and analyzes the image.

In some embodiments, the compact lens system 10 includes 16 sapphire, ball lenses (1 mm in diameter, refractive index of 1.77) integrated on top of a 4×4 array of oil-filled lens wells. The compact lens system 10 is placed directly on top of the haemocytometer. In some embodiments, to achieve good contact between the compact lens system 10 and the haemocytometer coverslip (and therefore eliminate any gap between them), a flexible cable can be used as a spring to push the compact lens system 10 against the coverslip. As a result, the distance between the compact lens system 10 and the sample in the Neubauer chamber is always fixed.

Counting RBCs

Figure 8A:
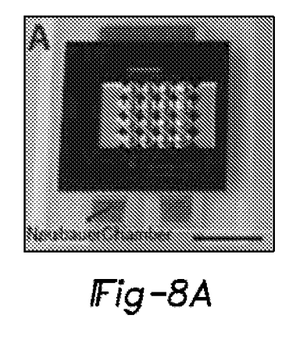
FIG. 8A is a plan view of the compact lens system on a Neubauer chamber.
Figure 8B:
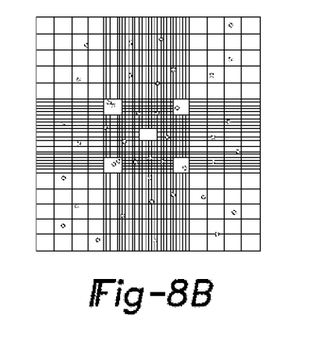
FIG. 8B is a schematic of a grid pattern below the compact lens system.

RBC counts were conducted with fresh whole, diluted blood samples on a commercial haemocytometer (Hausser Scientific) covered with a 150 μm thick glass coverslip (FIG. 8A). The Neubauer chamber of the haemocytometer had a total volume of 6-7 μl and had a square grid pattern to facilitate cell counting (FIG. 8B). To image the haemocytometer and count the RBCs, (i) a microscope (Olympus-BX51WI) in epi-illumination mode with a 50× objective (NA=0.5) was used that was connected to a 5 MP digital camera and, (ii) imaging system 100 with a field of view (FOV) of 200 μm and a NA of 0.54. In this case, the distance between the cells and bottom surface of the compact lens system 10 was ~250 μm (RBCs tend to settle at the bottom of the Neubauer chamber). In all our imaging experiments, a single lens was used from the compact lens system 10 for consistency in the image quality.

Blood samples (~10 μL in volume, diluted by a factor of 50, 100 and 200) were pipetted into the haemocytometer and driven in the Neubauer chamber by capillary action. Images of the blood samples were captured from 5 different 200 μm×200 μm square areas in the grid pattern of the Neubauer chamber (marked as dark boxes in FIG. 14B). The dilution and imaging procedures used in the present comparison are the recommended values for haemocytometer-based RBC counting.

Figure 9A:
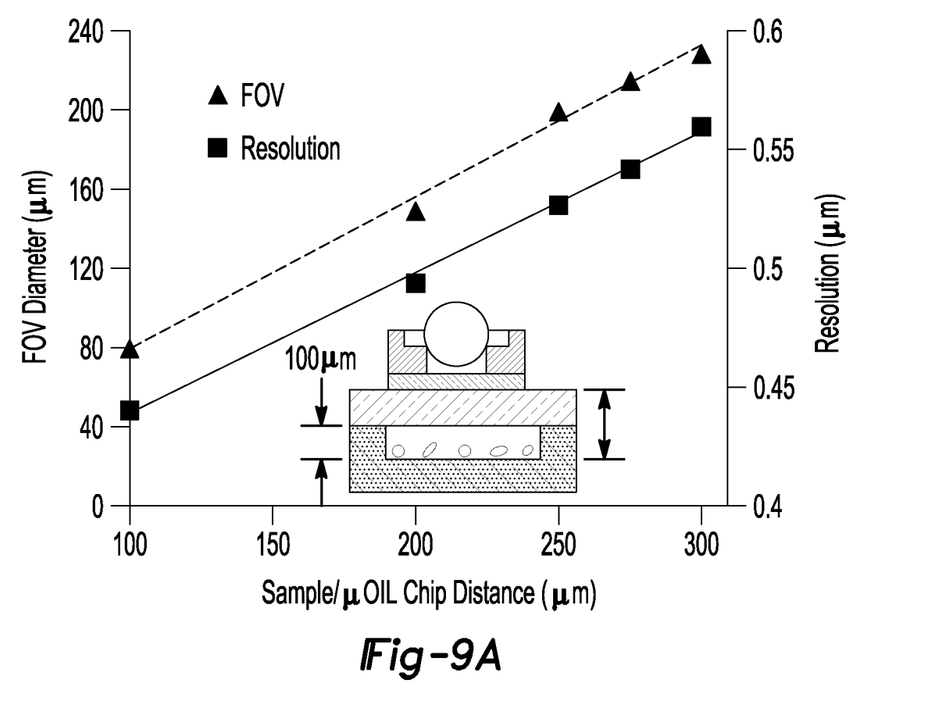
FIG. 9A is a graph illustrating field of view diameter and resolution versus the distance between the compact lens system and sample.

For cell counting applications, the field of view (FOV) of each lens 12 of compact lens system 10 is an important feature as it determines how much blood volume (and therefore how many cells) can be imaged. The FOV of compact lens system 10 can be modified by changing the distance between the bottom surface of compact lens system 10 and the sample 24/116. To estimate that dependence, we used the grid pattern of the Neubauer chamber as a reference sample, placed it at 100, 150, 175 and 200 μm below the bottom surface of the compact lens system 10 and measured the corresponding FOV. We used glass coverslips of different thicknesses to vary the distance between compact lens system 10 and sample 24/116. We also performed optical simulations in OSLO software to estimate the corresponding resolution (FIG. 9A).

Figure 9B:
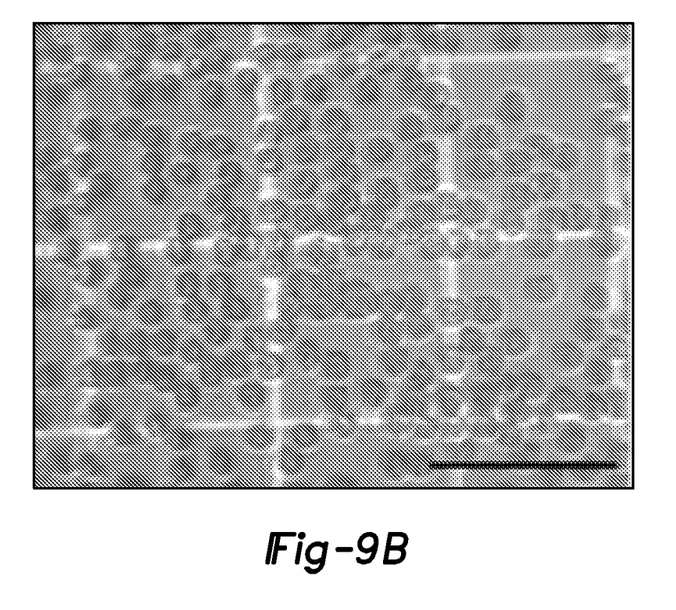
FIG. 9B is an image of red blood cells as captured by the compact lens system.

As expected, the larger the distance between compact lens system 10 and sample 24/116, the larger the FOV and lower the resolution. For our RBC counting experiments as explained earlier, we selected a FOV of ~200 μm as it matches the standardized, 200 μm×200 μm imaging area of the Neubauer chamber (depicted in FIG. 9B). The resolution and NA in this case were estimated to be 0.53 μm and 0.54, respectively.

Comparing RBC Counts

Figure 10A:
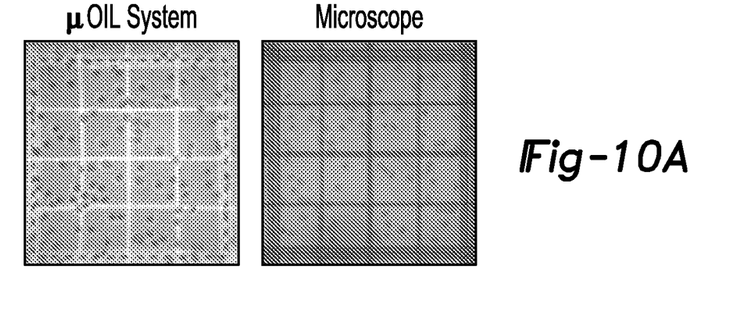
FIG. 10A is a comparison of images of diluted blood samples imaged by the compact lens system and a conventional microscope.
Figure 10B:
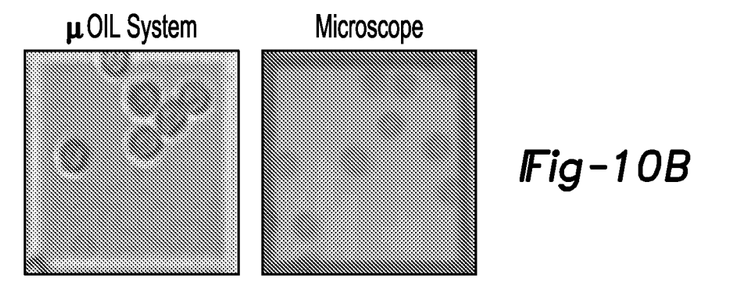
FIG. 10B is an enlarged comparison of the images of FIG. 10A.

We obtained images from diluted whole blood samples with compact lens system 10 and with a microscope (FIG. 10) as described earlier. In both cases, we used a haemocytometer with a 150 μm thick glass coverslip. It was determined that the NA of the compact lens system 10 and the microscope are similar (0.54 versus 0.5). The compact lens system 10 resolved details of the cell geometry/size as well as the microscope (FIG. 10B). The biconcave RBC shape with the characteristic dimple in the middle was clearly visible.

It is believed that the main reason for such a difference in image quality is due to the high contrast that is generated by the bright-field illumination of compact lens system 10. It was seen that the sapphire lens of compact lens system 10 distorts the edges of the viewing area. That effect, however, did not alter the RBC counting results as cells are still identifiable.

Figure 11:
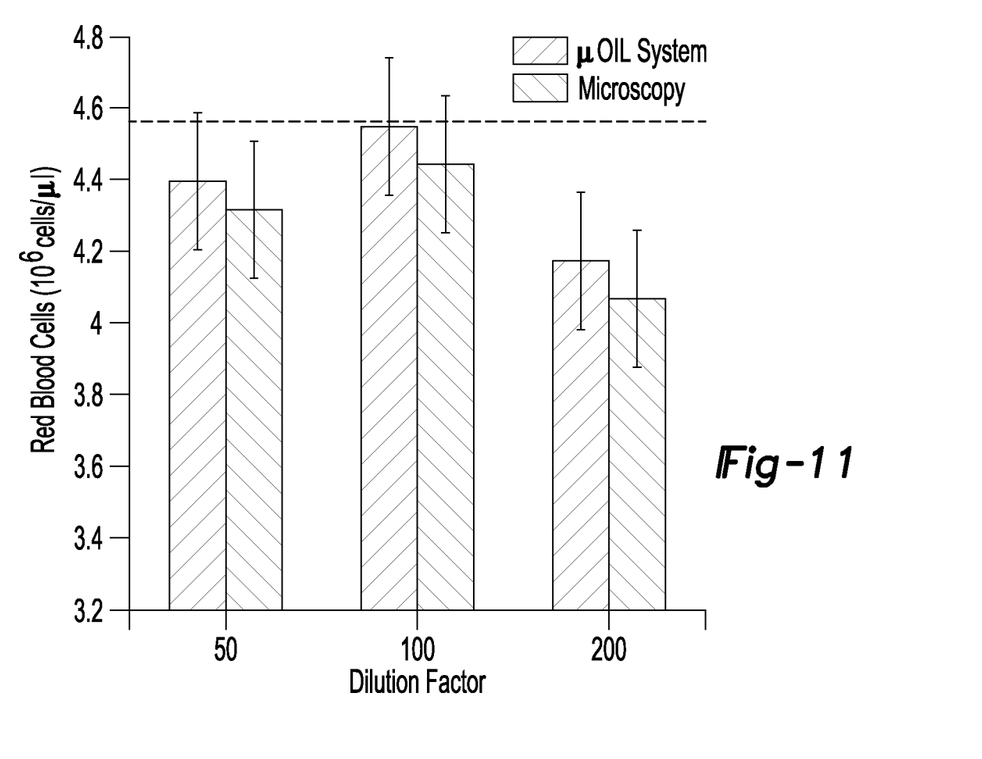
FIG. 11 is a graph comparing red blood cell counts of the compact lens system and a conventional microscope, with the dotted line representing the actual RBC count ($4.57 \times 10^6$ cells/mL)

Imaging was conducted at various blood sample dilutions by three different factors (50, 100 and 200) (FIG. 11). For all 3 dilution factors, no significant differences were observed between the RBC counts obtained with the microscope and compact lens system 10. The compact lens system 10 was also compared to a flow cytometer, which is considered the gold standard for cell counting applications. The flow cytometer count was 4.57 million cells/μL (see dotted line in FIG. 11, no dilution). The RBC count from compact lens system 10 is in good agreement with the flow cytometer results within one standard deviation for dilution factors of 50 and 100. RBC counts with larger (e.g. >200) dilution factors are not recommended as there is a significant difference (~10% error) between the flow cytometry and compact lens system 10 results. However, standard haemocytometer-based RBC counting procedures recommend a dilution factor of 200 to facilitate the manual counting process. We should also note that despite the fact that we used whole blood, the presence of white blood cells (WBCs) does not affect the RBC count as WBCs make up only 0.1% of the total number of cells in blood and as a result they rarely appear in the images.

We developed a high resolution, compact, single-cell imaging system for counting cells. The imaging capabilities of the system can be attributed to the use of a high NA microfabricated lens array. Although we demonstrated counting results from a single lens, we anticipate that the use of the entire lens array will automate the counting process and eliminate statistical variations as the sample size (number of cells counted) will significantly increase. It is believed that the use of compact lens system 10 is not limited to cell imaging/counting but it can be expanded to imaging other biological samples such as bacteria, microbes, microorganisms and tissue samples as it provides excellent image quality that is comparable to the one obtained from high end microscopes.

Fluorescence Imaging System: Total Internal Reflection (TIR)

Figure 12:
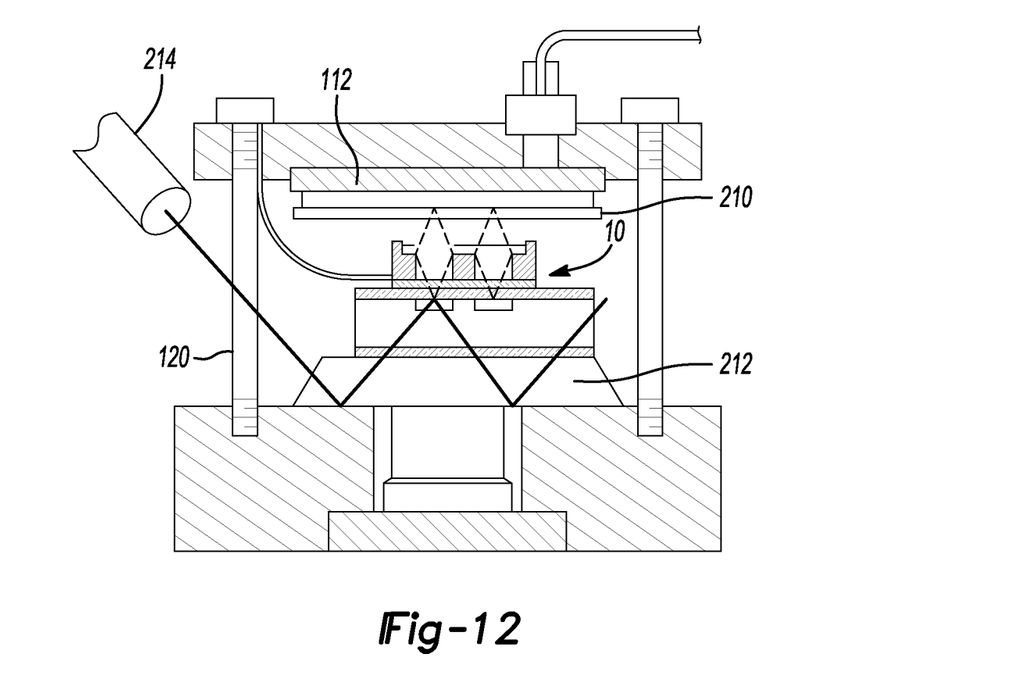
FIG. 12 is a schematic cross-sectional view of an imaging system employing the compact lens system and total internal reflection (TIR)

In some embodiments, a total internal reflection method can be used with compact lens system 10 and CMOS camera 112. The configuration of the system 200 is illustrated in FIG. 12. Long pass filter 210 is placed in front of the CMOS camera 112. A dove prism 212 is used to couple a blue laser light 214 to get total internal reflection. Critical angle (θc) is calculated from Sin−1 (n2/n1) to be 42 degrees assuming light propagates from prism (n2=1.52) to air (n1=1). The laser was attached to an xyz stage, and adjusted so that the angle of reflection is slightly above 42 degrees. The optical array, dove prism and microfluidic chip containing the biological sample are fixed, only the laser is moved and scanned in either direction (x or y example). Emitted fluorescent light is imaged by compact lens system 10 onto the CMOS camera 112.

Figure 13A:
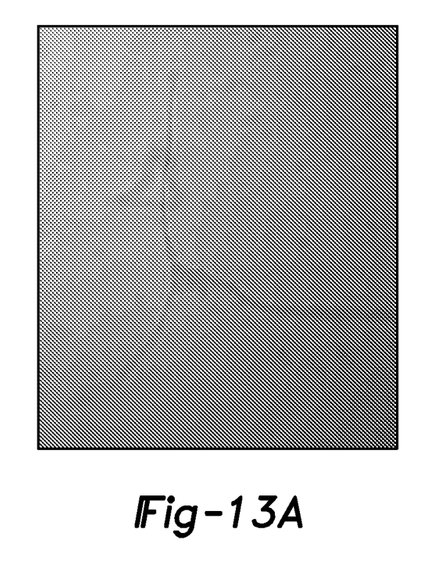
FIG. 13A is a bright field image of 4 μm fluorescent beads.
Figure 13B:
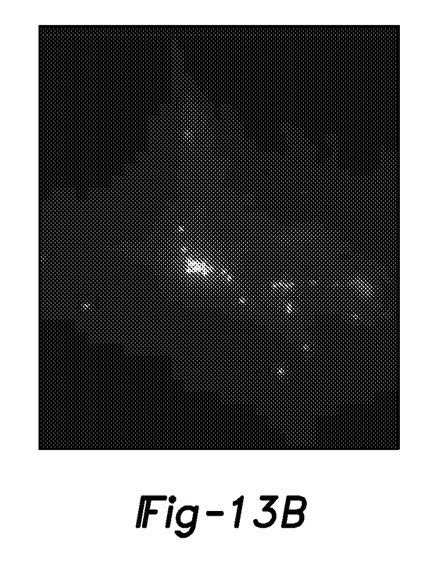
FIG. 13B is a TIR mode image of the same 4 μm fluorescent beads of FIG. 13A.

To test the TIR mode, 4 μm fluorescently labeled polystyrene spheres (PS) were used as sample. The image of PS taken by CMOS camera is illustrated in brightfield mode (FIG. 13A) using the blue LED below the sample chip and in TIR mode (FIG. 13B) using the blue laser outside the compact system.

Figure 14A:
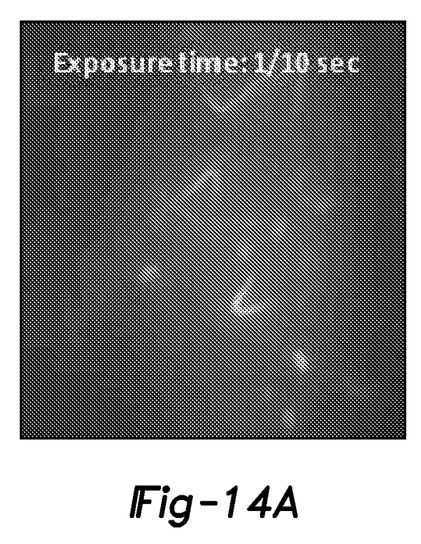
FIG. 14A is an image of C. elegans fluorescent transgenic lines.
Figure 14B:
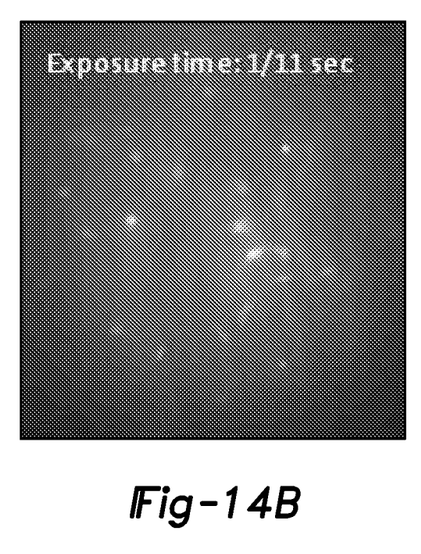
FIG. 14B is an image of fibroblast cells (10-15 μm) on glass substrate.

Biological samples such as *C. elegans* eggs and fibroblast cells are also demonstrated in FIGS. 14A and 14B. The capability of the compact lens system 10 is demonstrated further by image fluorescent of TNXL reporter of *C. elegan's* neuron ASH left and right.

CONCLUSIONS

According to the principles of the present teachings, a microfluidic-based oil-immersion lens chip with high NA, submicron resolution and wide field of view imaging capabilities is provided. The compact lens system 10 can be used as a stand-alone unit in lab-on-chip systems as or as an add-on accessory in low cost stereoscopes for various research and diagnostic biomedical applications.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A compact lens system for imaging a sample, said compact lens system comprising:
   a substrate having a well defining a first open portion having a first diameter and a second open portion having a second diameter, said second open portion being concentric with said first open portion and in communication therewith, said second diameter being less than said first diameter defining an edge therebetween;
   a transparent member adjacent said second open portion of said substrate, said transparent member enclosing said second open portion of said well;
   an index matching material being disposed in said well;
   a lens member being disposed in at least a portion of said first open portion and said second open portion of said well and in optical contact with said index matching material disposed in said well, a refractive index of said lens member being generally equal to a refractive index of said index matching material; and
   a spacer member extending from at least one of said substrate and said transparent member to define a spacing from a focal point of said lens member,
   wherein said lens member and said index matching material cooperate to image a sample disposed below said transparent member.

2. The compact lens system according to claim 1 wherein said refractive index of said index matching material is generally equal to a refractive index of said transparent member.

3. The compact lens system according to claim 1 wherein said index matching material is oil and said lens member is in fluid contact with said oil.

4. The compact lens system according to claim 1 wherein said index matching material is a liquid and said lens member is in fluid contact with said liquid.

5. The compact lens system according to claim 1 wherein said index matching material is a monomer that is polymerized within said well to form a solid polymer about at least a portion of said lens member.

6. The compact lens system according to claim 1 wherein said index matching material is a UV curable polymer that is cured within said well to form a solid polymer about at least a portion of said lens member.

7. The compact lens system according to claim 1 wherein said lens member has a refractive index in the range of 1.5 to 1.8 and said index matching material has a refractive index in the range of 1.3 to 1.8.

8. The compact lens system according to claim 1 wherein said lens member is a spherical lens.

9. The compact lens system according to claim 1 wherein a refractive index of said lens member is greater than 1.

10. The compact lens system according to claim 1, further comprising:
    a radiation source output radiation energy for imaging the sample.

11. The compact lens system according to claim 1, further comprising:
    a camera member operably coupled with said lens member for imaging the sample.

12. The compact lens system according to claim 1 wherein said substrate comprises a plurality of wells formed therein, each of said plurality of wells including said index matching material and said lens member.

13. The compact lens system according to claim 12, further comprising:
    a fluidic reservoir for containing at least a portion of said index matching material; and
    a fluidic channel fluidly coupling said fluidic reservoir to at least one of said plurality of wells.

14. The compact lens system according to claim 13 wherein said fluidic channel fluidly couples at least a portion of said plurality of wells in series.

15. A compact lens array system for imaging a sample, said compact lens array system comprising:
    a substrate having a plurality of microwells disposed in an array of rows and columns, each of the microwells defining a first open portion having a first diameter and a second open portion having a second diameter, said second open portion being concentric with said first open portion and in communication therewith, said second diameter being less than said first diameter defining an edge therebetween;
    a transparent member adjacent said second open portion of said substrate, said transparent member enclosing said second open portion of each of said microwells;
    a reservoir;
    a microfluidic channel fluidly coupling at least one row of said array of microwells to said reservoir;
    an index matching material being disposed in said reservoir and in fluid communication with said at least one row of said array of microwells via said microfluidic channel;
    a plurality of lens member each being disposed in at least a portion of said first open portion and said second open portion of each of said microwells in optical contact with said index matching material disposed in said microwells, a refractive index of each of said plurality of said lens member being generally equal to a refractive index of said index matching material; and a spacer member extending from at least one of said substrate and said transparent member to define a spacing from a focal point of said plurality of lens members, wherein said lens members and said index matching material cooperate to image a sample disposed below said transparent member.

16. The compact lens array according to claim 15 wherein said index matching material is oil and said lens member is in fluid contact with said oil.

17. The compact lens array according to claim 15 wherein said index matching material is a liquid and said lens member is in fluid contact with said liquid.

18. The compact lens array according to claim 15 wherein said lens member has a refractive index in the range of 1.5 to 1.8 and said index matching material has a refractive index in the range of 1.3 to 1.8.

19. The compact lens array according to claim 15, further comprising:

a fluidic reservoir for containing at least a portion of said index matching material; and a fluidic channel fluidly coupling said fluidic reservoir to at least one of said wells, wherein said fluidic channel fluidly couples a plurality of said wells in series.

\* \* \* \* \*